(12) United States Patent
Campbell et al.

(10) Patent No.: US 6,989,152 B1
(45) Date of Patent: Jan. 24, 2006

(54) COMPOUND FOR THE AMELIORATION OF PSEUDOFOLLICULITIS

(76) Inventors: John Campbell, 102 Natchez St., Starkville, MS (US) 39759; Charles Fox, 39-08 Tierney Pl., Fair Lawn, NJ (US) 07410

( * ) Notice: Subject to any disclaimer, the term of this patent is extended or adjusted under 35 U.S.C. 154(b) by 0 days.

(21) Appl. No.: 10/659,075

(22) Filed: Sep. 10, 2003

Related U.S. Application Data

(63) Continuation-in-part of application No. 10/191,265, filed on Jul. 8, 2002, now abandoned.

(51) Int. Cl.
*A61K 9/00* (2006.01)

(52) U.S. Cl. ............... 424/401; 424/78.06; 424/195.1; 514/844; 514/847; 514/848; 514/946; 514/947

(58) Field of Classification Search ............... 424/401, 424/78.06, 195.1; 514/844, 847, 848, 887, 514/946, 947
See application file for complete search history.

(56) References Cited

U.S. PATENT DOCUMENTS

| | | | |
|---|---|---|---|
| 1,550,026 A | 8/1925 | Goode |
| 2,876,164 A | 3/1959 | Wershaw |
| 4,014,995 A | 3/1977 | Juliano et al. |
| 4,201,235 A | 5/1980 | Ciavatta |
| 4,369,180 A | 1/1983 | Mihalovits |
| 4,488,564 A | 12/1984 | Grollier et al. |
| 4,505,902 A | 3/1985 | Millard |
| 4,525,344 A | 6/1985 | Tutsky |
| 4,548,728 A | 10/1985 | Franklin |
| 4,569,839 A | 2/1986 | Grollier et al. |
| 4,944,939 A | 7/1990 | Moore |
| 5,204,093 A | 4/1993 | Victor |
| 5,721,275 A | 2/1998 | Bazzano |
| 5,968,534 A | 10/1999 | Campbell |
| 6,228,379 B1 | 5/2001 | Campbell |
| 6,419,939 B2 | 7/2002 | Campbell |

*Primary Examiner*—Thurman K. Page
*Assistant Examiner*—Lakshmi Channavjjala
(74) *Attorney, Agent, or Firm*—Garvey, Smith, Nehrbass & North, LLC; Gregory C. Smith

(57) ABSTRACT

A compound for reducing the incidence of pseudofolliculitis combines a mild skin astringent, an oil based epidermal softener, and a hair stiffener. One embodiment of the compound combines refined powdered oatmeal and emollient of the compound combines refined powdered oatmeal and emollient oil, such as mink oil and liquid vitamin A in a petroleum jelly base. The mixture is applied by being massaged into the skin prior to lathering and then again immediately after the rinsing of the face after shaving. Continual usage significantly reduces the eruption of pseudofolliculitis. The compound would also include Borage Oil and Evening Primrose Oil rich in Gamma Linolenic Acid (GLA).

4 Claims, No Drawings

COMPOUND FOR THE AMELIORATION OF PSEUDOFOLLICULITIS

CROSS-REFERENCE TO RELATED APPLICATIONS

This is a continuation-in-part of co-pending U.S. patent application Ser. No. 10/191,265, filed Jul. 8, 2002 now abandoned, which is incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to skin treatment. More particularly, the present invention relates to a continuing skin treatment for topical application to the skin for amelioration and prevention of pseudofolliculitis.

2. General Background of the Invention

Pseudofolliculitis is a known condition, especially prevalent in persons having beards with a strong tendency to hair curling. It evinces itself after repeated beard shaving by inward growth of the beard hair into the skin and the subsequent formation of skin bumps with accompanying infection and eruptions.

It is a serious condition affecting a significant number of people, especially of African or Mediterranean descent, and has best been treated by restricting shaving by affected person.

Various treatments have been proposed for the amelioration of the adverse effect. These include U.S. Pat. No. 4,525,344, showing the use of a skin and beard conditioning compound, which is applied as part of the beard softening process (lathering) as a shaving aid. This patent is typical of the prior art in showing the use of a conditioning oil during the course of shaving.

Natural oils as a skin treatment providing a moist skin, including specifically the use of apricot kernel oil, avocado kernel oil and certain vitamins, including vitamin A, are shown in example in U.S. Pat. No. 4,505,902 or U.S. Pat. No. 4,201,235.

Various cosmetic preparations have been proposed utilizing fine oat flour as a binding and stabilizing agent; these include U.S. Pat. No. 4,014,995, and earlier patents showing the use of similar flours or pulverized plant substances as cohesion agents, such as U.S. Pat. No. 2,876,164 for soybean flour, U.S. Pat. No. 4,569,839 teaching generally pulverized plant substances, and U.S. Pat. No. 4,369,180 teaching cornstarch or cosmetic clay. In each of the patents the principal teaching is that the compound provides a binding agent performing a facial pack. There has been a continual use of oat flour dating back to U.S. Pat. No. 1,550,026, in which oat flour is shown as a binding agent for applying a skin astringent.

The emphasis in the prior art has been upon the teaching of an oil based softener for use as a shaving aid to ease the cutting of the beard. Prior art references and other references supporting the use of oils rich in GLA to treat dermatitis are attached in the accompanying Information Disclosure Statement.

BRIEF SUMMARY OF THE INVENTION

The invention discloses a continuing skin treatment for topical application to the skin for amelioration and prevention of pseudofolliculitis. The invention involves the repeated application of a petroleum jelly based mixture which contains, in combination, a skin astringent, a skin softening emollient oil and an oil designed to produce a relative stiffening of hair in the presence of the emollient oils, gamma linolenic acid in the form of either borage oil or evening primrose oil. The combination is intended to simultaneously;
  a) provide a mild astringent effect to the skin, causing an opening effect on the pores;
  b) provide a softening effect to the epidermal surface of the skin which is localized to the epidermal surface and which is specifically not equally seen in the hair follicles within the skin;
  c) provide a strengthening or stiffening effect to the hair follicles to counteract residual softening effects of the astringent and the emolument oils; and alleviate skin dermatitis.

In combination, the compound provides a continuing skin and hair tone environment in which the resistance of the skin to eruption of naturally curly hair is significantly reduced and at the same time the tendency of the hair to recurl and repenetrate is also reduced.

The material itself is not a shaving aid; in fact, to an extent it resists the effect of shaving in that it tends to stiffen the hairs of the beard, whereas a shaving aid is intended to soften the same. Rather, the material is a continuing skin treatment and is preferably applied by being massaged into the skin for a period of up to three days without shaving and then by being applied immediately prior to and then immediately after shaving. The material is additionally not a surface treatment in that it is massaged until it is absorbed into the skin and no excess material is left upon the skin.

It is therefore an object of the invention to disclose a compound of particular utility reducing the effects of pseudofolliculitis.

It is a further object of the invention to disclose a continuing skin treatment which reduces the incidence of pseudofolliculitis in an individual who is continually shaving.

It is a further object of the invention to provide a skin treatment which reduces the tendency of curly beard hairs to recurl into the skin.

It is a further object of the invention to disclose a skin treatment that reduces the incidence of naturally curly beard hairs from being trapped within the pores of the skin.

It is a further object of the invention to disclose a continuing skin treatment, reducing the effects of pseudofolliculitis, which may be applied to ameliorate the otherwise deleterious effect of normal shaving aids.

It is a further object to provide a skin treatment containing gamma linolenic acid (GLA) found in borage oil and evening primrose oil which when used topically, alleviates skin dermatitis, and alleviate the skin inflammation and irritation which accompanies this affection.

These and other objects of the invention may be more clearly seen from the detailed description of the preferred embodiment which follows.

DETAILED DESCRIPTION OF THE INVENTION

This invention relates to a compound to be applied and absorbed into the skin to ameliorate the effects of pseudofolliculitis which results as a side effect of shaving in affected individuals. Pseudofolliculitis is a skin condition resulting from shaving by persons who have naturally curly facial beard hair. In this particular condition the act of shaving cuts the hairs to a level slightly below the surface of the skin. The natural curvature of the hair causes the hair to curve in as it grows back. If the hair, instead of erupting from the skin, curves into the skin, an ingrown condition occurs which results in the formation of scars and pustules from the trapped ingrown hair.

The current invention is of a skin treatment compound which is applied and rubbed into the skin, and which reduces or ameliorates the effects of pseudofolliculitis from shaving by person susceptible to the condition.

The material comprises, in combination, a skin astringent, a skin emollient oil, and a hair stiffening agent, all in an absorbent jelled oil base, to be rubbed into the skin.

In a preferred embodiment of the invention a unit of the compound is made up as follows:
 a) The skin astringent is refined powdered oatmeal, such as, for example, Stero Pro™ Brand, in the amount of 250 grams;
 b) The emollient oil is a mixture consisting of:
  mink oil 300 grams
  apricot kernel oil 100 grams
  wheat germ oil 200 grams
 c. The hair strengthening agent is liquid vitamin A, 40 grams
 d. Gamma Linolenic Acid (GLA) in the form of Borage Oil and Evening Primrose Oil, in an amount between 0.5 and 20.0% of the compound mixture.
 d. All of the above is mixed in 850 grams of pure petroleum jelly to form an oil based gel; however, for purposes of the invention, the amount of each ingredient may vary depending on the circumstances.

In use the material is rubbed into the face until fully absorbed, twice a day, once immediately after shaving.

In the shaving process, the individual lathers and shaves in a normal manner. The face is then rinsed with cool water and towel dried, substantially free of surface moisture.

The second application of the mixture is immediately made to the dried face and rubbed into the skin until fully absorbed. This treatment is continuous.

An individual first starting the treatment, in addition, ceases shaving for at least three days, applying the material to the facial skin twice a day for the period before recommencing shaving.

It is to be noted that the material should be fully absorbed into the skin and thus is massaged until absorption is substantially complete. The refined powdered oatmeal is not a stiffening or caking agent, which is common use in cosmetics, but is an active ingredient of the material, and appears to have the desired skin astringent effect.

It is believed by the inventor that the material functions by creating a relative softening effect in the epidermal layer of the skin while at the same time producing a relative stiffening effect in the beard hairs of the fact. The latter effect counteracts the softening of the hair naturally induced by shaving aids as an incident of shaving. The softening to the epidermal layer of the skin reduces the resistance of the skin to passage of the hairs and is believed to reduce the tendency of the hair to be trapped within the pores of the skin. Likewise, the stiffening effect is believed to increase the tendency of the hair to erupt from the skin and reduce its tendency to curl over and be trapped into the pores.

The skin astringent then creates an opening effect on the pores and the three effects, in combination, reduce or eliminate the occurrence of pseudofolliculitis.

The Borage Oil and Evening Primrose Oil are rich in Gamma Linolenic Acid (GLA). It has been found that topical application of oils rich in GLA alleviate skin dermatitis. It has occurred to us that the addition of GLA rich oils to preparation used for testing Pseudofolliculitis Barbae would help alleviate the skin inflammation, irritation and dermatitis suffered by people with the affection. The GLA is most effective when included in the compound in an amount ranging from 0.5 to 20.0% GLA.

It is to be noted that the material as described is not a shaving aid but rather is a compound to provide a continuing skin and beard hair tone environment in which both the resistance of the skin to eruption of naturally curly hair and the tendency of the shaven hair follicles to recurl inwardly is significantly reduced.

In one test case, an individual with extensive visible pseudofolliculitis covering the chin, upper neck and both cheek areas, having an appearance of heavily mottled black scar tissue, visually extensive over the entire cheek, upper throat and upper chin area, followed the above described treatment. After a period of two weeks of usage, the skin eruptions had become visually imperceptive and the individual reported subjectively almost complete elimination of facial skin irritation.

Continued application of the treatment has permitted the individual to remain clean shaven without recurrence of the condition since.

In a second test, an individual having extensive visible scarring extending from below the windpipe up the neck to the chin was treated by stopping shaving and by twice daily (morning and evening) applications of the mixture for eight days. At this time, approximately 75% of the formerly affected skin area had cleared of visually perceptible bumps. Daily shaving then resumed, with one application in the manner above set forth immediately after shaving, and a second application applied to maintain the twice a day application schedule.

By the eleventh day only two visible bumps remained. In additional usage tests, users have uniformly reported subjective perception of reduced bumps, provided no skin cosmetics are used.

While only a specific formula as above described has been used in the tests, the invention extends to the slightly wider range of equivalents claimed in the broadest claim.

What is claimed is:

1. A composition for the amelioration of the effects of pseudofolliculitis, for topical application to the effected skin area consisting of:
 a) an absorbent skin astringent;
 b) an absorbent epidermal softening agent;
 c) an absorbent hair stiffening agent;
 d) gamma linolenic acid (GLA) wherein the GLA would be provided in the form of borage oil or evening primrose oil; and
 e) the entire as a mixture compounded in an oil based carrier for promoting absorption into the surface of the skin.

2. The composition in claim 1, wherein the gamma linolenic acid would be provided in an amount ranging between 0.5 and 20.0% of gamma linolenic acid.

3. A composition for topical application to the skin for the amelioration of the effects of pseudofolliculitis consisting of:
 a) an absorbent skin astringent in a quantity in excess of 20% of total compound
 b) an absorbent epidermal softening agent in a quantity of 30% of total compound;
 c) an absorbent hair stiffening agent in an effective amount of 1% in total compound;
 d) gamma linolenic acid (GLA) in an effective amount between 0.5 and 20.0% of the compound; and
 e) the entire as a mixture compounded in an oil based carrier for promoting absorption into the surface of the skin in an effective amount of approximately four parts in ten.

4. A method for the amelioration of the effects of pseudofolliculitis in a shaving individual comprising, in each 24 hour period of use;
 a) applying a quantity of the composition described in claim 3 above to the bearded area of the face;
 b) massaging said composition until a substantially complete absorption into the skin of the face occurs;
 c) shaving;
 d) rinsing the face with cool water;
 e) drying the face of all surface water;
 f) applying a quantity of the composition described in claim 3 above to the bearded area of the face; and
 g) massaging of said compound until substantially complete absorption into the skin of the face has occurred.

* * * * *